(12) United States Patent
Heider et al.

(10) Patent No.: US 8,992,915 B2
(45) Date of Patent: Mar. 31, 2015

(54) COMBINATION OF CD37 ANTIBODIES WITH ICE

(71) Applicants: Karl-Heinz Heider, Stockerau (AT); Anke Baum, Hinterbruehl (AT); Charlotte Astrid Russell, Hellerup (DK)

(72) Inventors: Karl-Heinz Heider, Stockerau (AT); Anke Baum, Hinterbruehl (AT); Charlotte Astrid Russell, Hellerup (DK)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/894,743

(22) Filed: May 15, 2013

(65) Prior Publication Data
US 2013/0309225 A1 Nov. 21, 2013

(30) Foreign Application Priority Data
May 16, 2012 (EP) .................................. 12168398

(51) Int. Cl.
| A61K 39/395 | (2006.01) |
| A61K 31/555 | (2006.01) |
| C07K 16/28 | (2006.01) |
| A61K 31/675 | (2006.01) |
| A61K 31/661 | (2006.01) |
| A61K 31/7048 | (2006.01) |
| A61K 39/00 | (2006.01) |

(52) U.S. Cl.
CPC ....... *A61K 39/3955* (2013.01); *A61K 2039/545* (2013.01); *A61K 31/555* (2013.01); *C07K 16/2896* (2013.01); *A61K 31/675* (2013.01); *A61K 31/661* (2013.01); *C07K 2317/565* (2013.01); *C07K 2317/56* (2013.01); *A61K 31/7048* (2013.01); *C07K 2317/24* (2013.01); *A61K 2039/505* (2013.01); *A61K 39/39558* (2013.01)
USPC ..................................................... 424/133.1

(58) Field of Classification Search
None
See application file for complete search history.

(56) References Cited

U.S. PATENT DOCUMENTS

| 5,500,362 | A | 3/1996 | Robinson et al. | |
| 6,020,153 | A | 2/2000 | Hardman et al. | |
| 6,461,824 | B1 | 10/2002 | Better et al. | |
| 6,548,640 | B1 | 4/2003 | Winter | |
| 8,333,966 | B2* | 12/2012 | Tan et al. .................. | 424/133.1 |
| 2003/0133939 | A1 | 7/2003 | Ledbetter et al. | |
| 2007/0020259 | A1 | 1/2007 | Hansen et al. | |
| 2007/0059306 | A1* | 3/2007 | Grosmaire et al. ........ | 424/144.1 |
| 2007/0237779 | A1 | 10/2007 | Ledbetter et al. | |
| 2009/0274692 | A1* | 11/2009 | Tan et al. .................. | 424/133.1 |
| 2010/0135900 | A1* | 6/2010 | Cerveny et al. .............. | 424/1.11 |
| 2010/0189722 | A1* | 7/2010 | Heider et al. .............. | 424/172.1 |
| 2011/0165153 | A1 | 7/2011 | Heider et al. | |
| 2012/0189618 | A1 | 7/2012 | Stilgenbauer et al. | |
| 2013/0236454 | A1 | 9/2013 | Stilgenbauer et al. | |
| 2013/0287797 | A1 | 10/2013 | Heider et al. | |
| 2013/0309224 | A1 | 11/2013 | Heider et al. | |
| 2014/0004110 | A1 | 1/2014 | Heider et al. | |
| 2014/0010808 | A1 | 1/2014 | Heider et al. | |

FOREIGN PATENT DOCUMENTS

| EP | 2295080 A2 | 3/2011 |
| WO | 03074679 A2 | 9/2003 |
| WO | 2004016753 A2 | 2/2004 |
| WO | 200517148 A1 | 2/2005 |
| WO | 2007014278 A2 | 2/2007 |
| WO | 2007041635 A2 | 4/2007 |
| WO | 2009019312 A2 | 2/2009 |
| WO | 2009023386 A2 | 2/2009 |
| WO | 2009126944 A2 | 10/2009 |
| WO | 2010011697 A1 | 1/2010 |
| WO | 2010057047 A1 | 5/2010 |
| WO | 2012007576 A1 | 1/2012 |

OTHER PUBLICATIONS

Andristos, L. et al., "A Phase 1 Trial of TRU-016, an Anti-CD27 Small Modular Immunopharmaceutical (SMIP TM) Protein in Relapsed and Refractory CLL: Early Promising Clinical Activity". Blood (ASH Annual Meeting Abstracts), 2009, 114, Abstract 3424 [retrieved from the internet: www.truemergent.com/wp-content/uploads/a_phase_1_trial_of_tru-016-ppt-final.pdf).

Andristos, L. et al., "A phase I trial of TRU-016, an anti-CD37 smaller modular immunopharmaceutical (SMIP) in relapsed and refractory CLL". 2009 ASCO Annual Meeting, Abstract No. 3017, Journal of Clinical Oncology, American Society of Clinical Oncology, U.S. vol. 27, No. 15s, Jan. 1, 2009.

Andritsos, L. et al., A Phase 1 Trial of TRU-016, An Anti-CED37 Small Modular Immunopharmaceutical (SMIP TM) Protein in Relapsed and Refractory CLL: Early Promising Clinical Activity. Bllod (ASH Annual Meeting Abstracts) 2009, 114: Abstract 3424 American Society of Hematology, vol. 114, No. 2, Dec. 8, 2009, p. 1330.

Bendig, Mary M. "Humanization of Rodent Monoclonal Antibodies by CDR Grafting" Methods: A Companion to Methods in Enzymology (1995) 8, pp. 83-93.

(Continued)

*Primary Examiner* — Sheela J Huff
(74) *Attorney, Agent, or Firm* — Michael P. Morris; David L. Kershner; Usha R. Patel

(57) ABSTRACT

The present invention relates to immunotherapies that are based on depletion of CD37-positive cells such as B-cells. The present invention provides methods for reduction of CD37-positive cells such as B-cells in an individual/patient using a combination of CD37 antibody/antibodies and ICE. The combination of CD37 antibodies and ICE is shown to have improved anti-tumor efficacy compared to single agent treatment. The application further provides materials and methods for treatment of diseases involving aberrant B-cell activity.

23 Claims, 2 Drawing Sheets

(56) References Cited

OTHER PUBLICATIONS

Boulianne, Gabrielle L., et al; Production of Functional Chimaeric Mouse/Human Antibody; Database Biosis (Online) Biosciences Information Service, Philadelphia, PA, US; (1984) vol. 312, No. 5995, pp. 643-646.

Braslawsky, Gary R. et al. "Adriamycin (hydrazone)-antibody conjugates require internalization and intracellular acid hydrolysis for antitumor activity" Cancer Immunology Immunotherapy (1991) 33: pp. 367-374.

Butler, T. et al., "Biologic and clinical significance of molecular profiling in Chronic Lymphocytic Leukemia". Blood Reviews, 24, 2010, p. 135-141.

Byrd, J.C. et al., "Chronic Lymphocytic Leukemia", Hematology, American Socienty of Hematology, Washington, DC, Jan. 1, 2004, p. 163-183.

Cerri, M. et al. Abstract 0410 "TP53 Mutations and Del17P13 Predict Similar Outcome and Chemorefractoriness in Chronic Lymphocytic Leukemia." Haematologica, 2008, 93(s1):163.

Chang, H. et al., "Aberrant Nuclear p53 Expression Predicts Hemizygous 17p (TP53) Deletion in Chronic Lymphocytic Leukemia." Am J Clin Pathol, 2010, vol. 133, pp. 70-74.

Dall'Acqua, William F. et al. "Antibody humanization by framework shuffling" Methods 36 (2005) pp. 43-60.

Fischer, Kirsten et al. "Bendamustine in Combination with Rituximab (BR) For Patients with Relapsed Chronic Lymphocytic Leukemia (CLL): A Multicentre Phase II Trials of the German CLL Study Group (GCLLSG)" Blood (ASH Annual Meeting Abstracts) 2008; 112 Abstract 330, 2 pgs.

Furman, R.R. et al., "Phase 1 Dose Escalation Study of TRU-016, An Anti-CD37 SMIP (TM) Protein in Relapsed and Refractory CLL", Blood, American Society of Hematology, US, vol. 116, No. 21, Dec. 7, 2010, p. 31-32.

GenBank Accession ABJ97713, Anti-human CD37 mAb G28-1 immunoglobulin heavy chain variable region [*Mus musculus*], Aug. 1, 2007.

Gribben, J. G. "blood—How I treat CLL up front". Blood Journal, vol. 115, No. 2, Jan. 14, 2010, p. 186-197.

Hallek, M. et al., "Guidelines for the Diagnosis and Treatment of Chronic Lymphocytic Leukemia: A Report from the International Workshop on Chronic Lymphocytic Leukemia Updating the National Cancer Institute—Working Group 1996 Guidelines." Blood, 2008, vol. 111, No. 12, pp. 5446-5456.

Heider, Karl-Heinz et al. "A novel Fc-engineered monclonal antibody to CD37 with enhanced ADCC and high proapoptotic activity for treatment of B-cell malignancies" Blood (2011) 118, pp. 4159-4168.

International Search Report for PCT/EP2008/060464 mailed Feb. 26, 2009.

International Search Report for PCT/EP2011/062133 mailed Nov. 4, 2011.

Kienle, D. et al., "Gene expression factors as predictors of genetic risk and survival in chronic lymphocytic leukemia". Haematologica—The Hematology Journal, vol. 95, No. 1, Jan. 2010, p. 102-109.

Laurenti, L. et al., "New and Old Monoclonal Antibodies for the Treatment of Chronic Lymphocytic Leukemia". Mini Reviews in Medicinal Chemistry, Bentham Science Publishers, Hilversum, NL, vol. 11. No. 6, Jan. 1, 2011, p. 508-518.

Maddipatia, S. et al., "Augmented Anti-tumor Activity against B-Cell Lymphoma by a Combination of Monoclonal Antibodies Targeting TRAIL-R1 and CD20", Clinical Cancer Research, 2007, 13, p. 4556-4564.

Mohr, J. et al., Abstract 3119 "The Response to DNA Damage in CLL Cells is Partly Determined by the Type of TP53 Mutation and Genomic Aberrations." 2008, 112.

Montserrat, E. et al., "How I Treat Refractory CLL." Blood, 2006, vol. 107, No. 4, pp. 1276-1283.

NCBI GenBank Accession: AAB17008, Hu, W.X et al., "Comparison of NPC Transforming Gene Tx to Ig Kappa Constant Region Gene and Their Expresion in Different Cell Lines". Oct. 14, 1996.

NCBI GenBank Accession: CAC20454. McLean, G.R. et al., "Human and murine immunoglobulin expression vector cassettes", Feb. 9, 2001.

NCBI, GenBank Accession: ABJ97712. Ledbetter, J.A., et al., "Monoclonal antibodies to a new gp40-45 (CD37) B cell associated cluster group modulate B cell proliferation". Aug. 1, 2007.

Office Action—Final Rejection mailed Mar. 6, 2013. U.S. Appl. No. 12/672,378, filed Apr. 14, 2010.

Office Action mailed Mar. 6, 2013; U.S. Appl. No. 12/884,563, filed Sep. 17, 2010.

Office Action mailed May 31, 2012; U.S. Appl. No. 12/672,378, filed Apr. 14, 2010.

Office Action mailed Oct. 30, 2012; U.S. Appl. No. 12/672,378, filed Apr. 14, 2010.

Paul, W.E., Fundamental Immunology, 3rd Edition, 1993, pp. 292-295.

Presta, Leonard G. "Engineering of therapeutic antibodies to minimize immunogenicity and optimize function" Advanced Drug Delivery Reviews 58 (2006) pp. 640-656.

Qu, Q. et al., "Construction and Expression of Human-Mouse Chimeric Antibody against Human CD40", Journal of Cellular and Molecular Immunology (Chin J. Cell Mol Immunolo), 2006, 22(2), 189-192.

Rossi, D. et al., Abstract 3137 "The Prognostic Value of TP53 Mutations in Chronic Lymphocytic Leukemia (CLL) Is Independent of del17p13: Implications for Overall Survival and Chemorefractoriness." 2008, vol. 112.

Rudikoff, Stuart et al. "Single amino acid substitution altering antigen-binding specificity" Proc., Natl. Acad. Sci. (1982) vol. 79, pp. 1979-1983.

Rummel, Mathias J. "German Experience with Bendamustine Treating Relapsed/Refractory Indolent B-Cell and Mantle Cell Lymphomas" (2007) Seminars in Hematology, pp. S22-S26.

Rummel, Mathias J. et al. "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)" Blood (ASH Annual Meeting Abstracts) 2007: 110: Abstract 385, 2 pgs.

Tsurushita, Naoya et al. "Design of humanized antibodies: From anti-Tac to Zenapax" Methods 36 (2005) pp. 69-83.

WO2005/017148-A1—Part 1 of 2—"Binding Constructs and Methods for Use Thereof". Applicant: Trubion Pharmaceuticals, Inc. International Publication date: Feb. 24, 2005.

WO2005/017148-A1—Part 2 of 2—"Binding Constructs and Methods for Use Thereof". Applicant: Trubion Pharmaceuticals, Inc. International Publication date: Feb. 24, 2005.

Zenz, T, et al., "Detailed analysis of p53 pathway defects in fludarabine-refractory chronic lymphocytic leukemia (CLL): dissecting the contribution of 17p deletion, TP53 mutation, P53-p21 dysfunction, and miR34a in a prospective clinical trial". Blood, vol. 114, No. 13, Sep. 2009, p. 2589-2597.

Zenz, T. et al. "In Vitro Activity of Type II anti-CD20 Anitbody GA101 in Refractory, Genetic High-Risk CLL". Blood (ASH Annual Meeting Abstracts), 2009, 114: Abstract 2379.

Zenz, T. et al., "Exceptional In Vitro Activity of CD37 Antibodies in CLL". Blood (ASH Annual Meeting Abstracts), Abstract 2460, vol. 116, No. 21, Dec. 7, 2010, p. 1021-1022.

Zenz, T. et al., "From pathogenesis to treatment of chronic lymphocytic leukemia". Nature Reviews/Cancer, vol. 10, Jan. 2010, p. 37-50.

Zenz, T. et al., "Monoallelic TP53 Inactivation is Associated with Poor Prognosis in Chronic Lymphocytic Leukemia: Results from a Detailed Genetic Characterization with Long-term Follow-up." Blood, 2008, vol. 112, No. 8, pp. 3322-3329.

Zenz, T. et al., Abstract 782 "17p Deletion in CLL: Detailed Analysis of TP53 Mutations, Alternative Mechanisms of p53 Inactivation, Clone Size and Clonal Evolution." 2008, 112.

(56) References Cited

OTHER PUBLICATIONS

Zhao, Z. et al., "Targeting CD37-positive lymphoid malignancies with a novel engineered small modular immunopharmaceutical". Blood, Oct. 1, 2007, LNKD-Pubmed:17440052, vol. 110, No. 7, p. 2569-2577.

Zucca, Emanuele et al. "Addition of rituximab to chlorambucil produces superior event-free survival in the treatment of patients iwth extranodal marginal-zone-B-cell lymphoma: 5 year analysis of the IELSG-19 Randonmized Study" AN: NLM23295789, Database Medline (2013) 2 pgs.

* cited by examiner

SEQUENCE LISTING

```
<160> NUMBER OF SEQ ID NOS: 21

<210> SEQ ID NO 1
<211> LENGTH: 348
<212> TYPE: DNA
<213> ORGANISM: Mus musculus

<400> SEQUENCE: 1
gcggtccagc tgcagcagtc tggacctgag ctggaaaagc ctggcgcttc agtgaagatt      60
tcctgcaagg cttctggtta ctcattcact ggctacaata tgaactgggt gaagcagaat     120
aatggaaaga gccttgagtg gattggaaat attgatcctt attatggtgg tactacctac     180
aaccggaagt tcaagggcaa ggccacattg actgtagaca atcctccag cacagcctac      240 atgcagctca agagtctgac atctgaggac tctgcagtct attactgtgc aagatcggtc     300
ggccctatgg actactgggg tcaaggaacc tcagtcaccg tctcttct                  348

<210> SEQ ID NO 2
<211> LENGTH: 116
<212> TYPE: PRT
<213> ORGANISM: Mus musculus

<400> SEQUENCE: 2

Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Val Gly Pro Met Asp Tyr Trp Gly Gln Gly Thr Ser Val
            100                 105                 110

Thr Val Ser Ser
        115

<210> SEQ ID NO 3
<211> LENGTH: 324
<212> TYPE: DNA
<213> ORGANISM: Mus musculus

<400> SEQUENCE: 3
gacatccaga tgactcagtc tccagcctcc ctatctgcat ctgtgggaga gactgtcacc      60
atcacatgtc gaacaagtga aaatgtttac agttatttgg cttggtatca gcagaaacag     120
ggaaaatctc ctcagctcct ggtctctttt gcaaaaacct tagcagaagg tgtgccatca     180
```

```
aggttcagtg gcagtggatc aggcacacag ttttctctga agatcagcag cctgcagcct    240
gaagattctg gaagttattt ctgtcaacat cattccgata atccgtggac gttcggtgga    300
ggcaccgaac tggagatcaa acga                                           324
```

<210> SEQ ID NO 4
<211> LENGTH: 108
<212> TYPE: PRT
<213> ORGANISM: Mus musculus

<400> SEQUENCE: 4

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Arg
            100                 105
```

<210> SEQ ID NO 5
<211> LENGTH: 446
<212> TYPE: PRT
<213> ORGANISM: Artificial Sequence
<220> FEATURE:
<223> OTHER INFORMATION: Description of Artificial Sequence: Synthetic
      construct heavy chain A2 polypeptide

<400> SEQUENCE: 5

```
Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Val Gly Pro Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      construct light chain A2 polypeptide

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
            35                  40                  45

Ser Phe Ala Lys Thr Leu Ala Glu Gly Val Pro Ser Arg Phe Ser Gly
            50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
```

```
                    85                  90                  95
Thr Phe Gly Gly Gly Thr Glu Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      construct constant heavy chain polypeptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      construct constant light chain polypeptide

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 9
<211> LENGTH: 446
<212> TYPE: PRT
<213> ORGANISM: Artificial Sequence
<220> FEATURE:
<223> OTHER INFORMATION: Description of Artificial Sequence: Synthetic
      construct heavy chain A4 polypeptide

<400> SEQUENCE: 9

Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
            35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
65                  70                  75                  80
```

```
Met Gln Leu Lys Ser Leu Thr Ser Glu Asp Ser Ala Val Tyr Tyr Cys
                 85                  90                  95

Ala Arg Ser Val Gly Pro Met Asp Tyr Trp Gly Gln Gly Thr Ser Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
            210                 215                 220

Cys Pro Pro Cys Pro Ala Pro Glu Leu Leu Ala Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      construct light chain A4 polypeptide

<400> SEQUENCE: 10
```

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 446
<212> TYPE: PRT
<213> ORGANISM: Artificial Sequence
<220> FEATURE:
<223> OTHER INFORMATION: Description of Artificial Sequence: Synthetic
      construct heavy chain B2 polypeptide

<400> SEQUENCE: 11

Ala Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Gly Thr Thr Tyr Asn Arg Lys Phe
50                  55                  60

Lys Gly Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
                130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      construct light chain B2 polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
                20                  25                  30

Leu Ala Trp Tyr Gln Gln Lys Pro Gly Lys Ala Pro Lys Leu Leu Val
                35                  40                  45
```

```
Ser Phe Ala Lys Thr Leu Ala Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln His His Ser Asp Asn Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 13
<211> LENGTH: 446
<212> TYPE: PRT
<213> ORGANISM: Artificial Sequence
<220> FEATURE:
<223> OTHER INFORMATION: Description of Artificial Sequence: Synthetic
      construct heavy chain B4 polypeptide

<400> SEQUENCE: 13

Ala Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Thr Gly Tyr
             20                  25                  30

Asn Met Asn Trp Val Arg Gln Ala Pro Gly Gln Gly Leu Glu Trp Met
         35                  40                  45

Gly Asn Ile Asp Pro Tyr Tyr Gly Gly Thr Thr Tyr Asn Arg Lys Phe
     50                  55                  60

Lys Gly Arg Val Thr Leu Thr Val Asp Lys Ser Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Val Gly Pro Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Ala Gly Pro Asp Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 14
<211> LENGTH: 214
<212> TYPE: PRT
<213> ORGANISM: Artificial Sequence
<220> FEATURE:
<223> OTHER INFORMATION: Description of Artificial Sequence: Synthetic
      construct light chain B4 polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
            35                  40                  45

Ser Phe Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His His Ser Asp Asn Pro Trp
            85                  90                  95

Thr Phe Gly Gln Gly Thr Lys Val Glu Ile Lys Arg Thr Val Ala Ala

-continued

```
                  100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      CDR1 heavy chain (H1) peptide

<400> SEQUENCE: 15

Gly Tyr Asn Met Asn
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR2 heavy chain (H2) peptide

<400> SEQUENCE: 16

Asn Ile Asp Pro Tyr Tyr Gly Gly Thr Thr Tyr Asn Arg Lys Phe Lys
1               5                   10                  15

Gly

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR3 heavy chain (H3) peptide

<400> SEQUENCE: 17

Ser Val Gly Pro Met Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR1 light chain (L1) peptide

<400> SEQUENCE: 18

Arg Thr Ser Glu Asn Val Tyr Ser Tyr Leu Ala
```

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR2 light chain (L2) peptide

<400> SEQUENCE: 19

Phe Ala Lys Thr Leu Ala Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR3 light chain (L3) peptide

<400> SEQUENCE: 20

Gln His His Ser Asp Asn Pro Trp Thr
1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      alternative CDR2 heavy chain (H2b) peptide

<400> SEQUENCE: 21

Asn Ile Asp Pro Tyr Tyr Gly Gly Thr Thr Tyr Asn Arg
1               5                   10
```

COMBINATION OF CD37 ANTIBODIES WITH ICE

TECHNICAL FIELD

The present invention relates to immunotherapies that are based on depletion of CD37-positive cells such as B-cell cells. In particular, the present invention relates to a combination of CD37 antibodies, especially A2 and B2, with chemotherapy, especially ICE for use in such therapies, e.g. in the treatment of B-cell malignancies, other CD37-positive malignancies, and autoimmune conditions.

BACKGROUND OF THE INVENTION

Immunotherapy using monoclonal antibodies (mAbs) has emerged as a safe and selective method for the treatment of cancer and other diseases. In particular, the role of monoclonal antibodies in therapies that are based on B-cell depletion, e.g. in the treatment of B-cell malignancies, has expanded since the introduction of rituximab (Rituxan®), an antibody that is directed against the CD20 antigen on the B-cell surface. Numerous studies have confirmed the efficacy of rituximab as a single agent and in combination therapy in low-grade NHL. Frontline therapy with rituximab added to the combination of cyclophosphamide, doxorubicin, vincristine, and prednisolone (CHOP) significantly improves the outcome for patients with advanced-stage follicular lymphoma compared with therapy with CHOP alone (Hiddemann W, et al. Blood 2005; 106: 3725-3732 (2005)). The addition of rituximab to a combination of fludarabine, cyclophosphamide, mitoxantrone (FCM) significantly increases the response rate and prolongs survival as compared with FCM alone in patients with relapsed and refractory follicular and mantle cell lymphomas (Forstpointner R, et al., Blood, 2004; 104: 3064-3071).

However, only a subset of patients responds to therapy and the majority of those eventually relapse following rituximab treatment. Therefore, there is a need to find immunotherapies with higher efficacy than antibodies that are directed against the CD20 antigen (e.g. rituximab).

SUMMARY OF THE INVENTION

The invention describes CD37 antibodies, preferably A2 and B2, used in combination with a combination chemotherapy regimen employing three drugs: ifosfamide, carboplatin, and etoposide (or etoposide phosphate) abbreviated as "ICE". This combination of CD37 antibodies, preferably A2 and B2, with ICE surprisingly results in an improved anti-tumor effect. The two therapeutic agents, CD37 antibody and ICE, may be administered simultaneously, optionally as a component of the same pharmaceutical preparation, or ICE may be administered before or after administration of the CD37 antibody.

In accordance with the invention, there are provided novel combinations of anti-CD37 antibodies as described in the present invention with ICE. Accordingly, the combination of anti-CD37 antibodies of the present invention and ICE are used to treat patients suffering from CD37-positive malignancies, e.g. B-cell malignancies.

A high degree of tumor growth retardation in patients with B-cell malignancies, e.g. CLL and B-NHL, is considered advantageous for the treatment of those patients and is considered to translate into increased clinical benefit for patients treated with such an agent. CD37 antibodies such as A2 in combination with ICE display a high degree of tumor growth retardation in a Ramos lymphoma model in vivo. The anti-tumor effect of the combination of CD37 mAb and ICE is superior to the effect of the individual agents alone (see data disclosed in this application). Tumor growth retardation is considered a surrogate parameter for treatment efficacy. This superior efficacy of A2 in combination with ICE is especially evident in FIGS. 1 and 2 and is superior to that of the individual agents alone.

The benefit of a combination treatment with CD37 antibodies, especially mAbs A2 or B2, and chemotherapy such as ICE is further demonstrated in clinical trials, which compare the efficacy of ICE monotherapy against the efficacy of a combination of ICE and CD37 antibodies, especially mAb A2 or B2. The trial is performed in a randomized fashion, e.g. the patients are assigned to the two different treatment arms of the study by randomization. The response to treatment is defined by standardized response criteria for the respective indication. The efficacy of the treatment is assessed by surrogate parameters like progression free survival (PFS) or response rate. A clinically relevant therapeutic effect is for example the increase in complete response rate by 50% with ICE and A2 or B2 compared to ICE alone (e.g. 45% compared to 30%) for patients with CD37-positive malignancies like mature B-cell malignancies, e.g. relapsed B-NHL.

Furthermore, the benefit of a combination treatment with CD37 antibodies, especially mAbs A2 or B2, a chemotherapy such as ICE, and a CD20 antibody such as Rituximab is further demonstrated in clinical trials, which compare the efficacy of ICE administered in combination with anti-CD20 antibody (e.g. Rituximab), which is referred to as R-ICE, against the efficacy of a combination of ICE administered in combination with anti-CD20 antibody and additionally CD37 antibody, especially mAb A2 or B2. Such a trial is performed in a randomized fashion, e.g. the patients are assigned to the two different treatment arms of the study by randomization. The response to treatment is defined by standardized response criteria for the respective indication. The efficacy of the treatment is assessed by surrogate parameters like progression free survival (PFS) or response rate. A clinically relevant therapeutic effect is for example increase in complete response rate by 50% with R-ICE and A2 or B2 compared to R-ICE alone (e.g. 45% compared to 30%) for patients with CD37 positive malignancies like mature B-cell malignancies, e.g. relapsed B-NHL.

To be used in therapy, the CD37 antibody is included into pharmaceutical compositions appropriate to facilitate administration to animals or humans. Typical formulations of the CD37 antibody molecule can be prepared by mixing the CD37 antibody molecule with physiologically acceptable carriers, excipients or stabilizers, in the form of lyophilized or otherwise dried formulations or aqueous solutions or aqueous or non-aqueous suspensions.

Pharmaceutically acceptable carriers and adjuvants for use with CD37 antibodies according to the present invention include, for example, ion exchangers, alumina, aluminum stearate, lecithin, serum proteins, buffer substances, water, salts or electrolytes and cellulose-based substances.

Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g. Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function. This is not a complete list of possible pharmaceutically acceptable carriers and adjuvants, and one of ordinary skilled in the art would know other possibilities, which are replete in the art.

In one embodiment the CD37 antibody A2 is formulated in a vehicle containing 25 mM Na-citrate, 115 mM NaCl and 0.04% Tween 80, pH 6.0 and diluted with PBS.

The CD37 antibody molecules may also be dried (freeze-dried, spray-dried, spray-freeze dried, dried by near or super-critical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are known in the art.

Naturally, the pharmaceutical compositions/formulations to be used for in vivo administration must be sterile; sterilization may be accomplished be conventional techniques, e.g. by filtration through sterile filtration membranes.

It may be useful to increase the concentration of the CD37 antibody to come to a so-called high concentration liquid formulation (HCLF); various ways to generate such HCLFs have been described.

The CD37 antibody molecule may also be contained in a sustained-release preparation. Such preparations include solid, semi-solid or liquid matrices of hydrophobic or hydrophilic polymers, and may be in the form of shaped articles, e.g. films, sticks or microcapsules and may be applied via an application device. Examples of sustained-release matrices include polyesters, hydrogels (for example, poly(2-hydroxyethyl-methacrylate) or sucrose acetate butyrate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilization from acidic solutions, controlling moisture content, using appropriate additives, and developing specific polymer matrix compositions.

The CD37 antibody molecule, especially A2 and B2, can be incorporated also in other application forms, such as dispersions, suspensions or liposomes, tablets, capsules, powders, sprays, transdermal or intradermal patches or creams with or without permeation enhancing devices, wafers, nasal, buccal or pulmonary formulations, or may be produced by implanted cells or—after gene therapy—by the individual's own cells.

A CD37 antibody molecule, especially A2 and B2, may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

The preferred mode of application is parenteral, by infusion or injection (intravenous, intramuscular, subcutaneous, intraperitoneal, intradermal), but other modes of application such as by inhalation, transdermal, intranasal, buccal, oral, may also be applicable.

For therapeutic use, the compounds may be administered in a therapeutically effective amount in any conventional dosage form in any conventional manner. Routes of administration include, but are not limited to, intravenously, intramuscularly, subcutaneously, intrasynovially, intrathecally by infusion, sublingually, transdermally, orally, topically or by inhalation, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). A therapeutically effective amount can be determined by a skilled artisan based upon such factors as weight, metabolism, and severity of the affliction etc.

Preferably the active compound is dosed at about 0.01 µg to about 500 mg per kilogram of body weight at least once per treatment cycle, e.g. on a weekly basis (0.01 µg to 500 mg per kilogram of body weight). More preferably the active compound is dosed at about 0.01 mg to 40 mg per kilogram of body weight at least once per treatment cycle.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 0.01 µg/kg to 40 mg/kg of CD37 antibody, especially of A2 and B2, is an initial candidate dosage for administration to the patient, whether, for example, by one or more separate administrations, or by infusion such as continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays, e.g. by determining the extent of B-cell depletion (e.g. using flow cytometry).

For A2 (CD37 antibody comprising SEQ ID Nos:5 and 6), the estimated dose for a 70 kg human is in the range of 1 mg to 2800 mg, preferably 1 mg to 1400 mg, or 10 mg to 1400 mg, or 10 mg to 1000 mg, or 100 mg to 1400 mg, or 100 mg to 385 mg, most preferably 10 mg to1400 mg. Said dose is preferably a weekly dose. A dose range of 1 mg to 2800 mg or 2 mg to 800 mg or more specifically 200 mg to 770 mg for a 70 kg human is preferred, if A2 is administered every two weeks. The estimated human dose of B2 (CD37 antibody comprising SEQ ID Nos:11 and 12) for a 70 kg human is in the range of 1 mg to 2800 mg, preferably in the range of 1 mg to 1400 mg or 10 mg to 1400 mg, or 10 mg to 1000 mg, or 100 mg to 1400 mg, or more specifically 100 mg to 385 mg. Said dose is preferably a weekly dose. A dose range of 1 mg to 2800 mg or 2 mg to 800 mg or more specifically 200 mg to 770 mg for a 70 kg human is preferred, if B2 is administered every two weeks.

Treatment cycle: The treatment cycle is a time period of between 1 to 6 weeks, preferably 2 to 4 weeks, most preferably 3 weeks, wherein the patient receives at least one dose of the CD37 antibody and at least one dose of ICE.

ICE is preferably dosed on three consecutive days of a treatment cycle, which is preferably 2-3 weeks (14-21 days) long. The doses of each component of ICE range for 1) ifosfamide between 3-7 g/m2 (preferably 5 g/m2) body surface given on $2^{nd}$ treatment day, 2) carboplatin between 200-800 mg (dose is based on clearance and area under curve (AUC)) given on $2^{nd}$ treatment day and 3) etoposide between 50-200 mg/m2 (preferably 100 mg/m2) given on $1^{st}$, $2^{nd}$ and $3^{rd}$ treatment day.

For the treatment of a NHL patient ICE is preferably administered in treatment cycles, whereby a treatment cycle is preferably 2-4 weeks (14 to 28 days) or 2-3 weeks (14-21 days) long, most preferably 3 weeks (21 days).

In another treatment cycle scheme ICE is given together with Rituximab or another antibody targeting CD20. This treatment option is referred to as R-ICE. In a preferred treatment cycle scheme for R-ICE the Rituximab (or alternatively any other antibody targeting CD20) is embedded into the ICE treatment cycle and dosing scheme (schemes/treatment cycles as described in the paragraph above), preferably by administering the antibody targeting CD20 (e.g. Rituximab) together with etoposide on the $1^{st}$ treatment day. A preferred dose for Rituximab is 100-500 mg/m$^2$ body surface, preferably 375-500 mg/m$^2$, most preferably 375 mg/m$^2$.

For CD37 combination therapy during the ICE or R-ICE treatment cycle at least one CD37 antibody, preferably A2 or B2, is administered at a dose as described above either before, after, or simultaneously with the ICE or R-ICE administration. Simultaneously hereby means on the same days. Furthermore, another preferred treatment cycle scheme for NHL comprises additional administration(s) of CD37 antibody in-between, for example in the middle of the treatment cycle at about 2 weeks.

The "therapeutically effective amount" of the antibody to be administered is the minimum amount necessary to prevent, ameliorate, or treat a disease or disorder.

CD37-positive malignancies include, without limitation, all malignancies that express CD37. B-cell malignancies belong to the group of CD37-positive malignancies. B-cell malignancies include, without limitation, B-cell lymphomas (e.g. various forms of Hodgkin's disease, B-cell non-Hodgkin's lymphoma (NHL) and related lymphomas (e.g. Waldenström's macroglobulinaemia (also called lymphoplasmacytic lymphoma or immuno-cytoma) or central nervous system lymphomas), leukemias (e.g. acute lymphoblastic leukemia (ALL), chronic lymphocytic leukemia (CLL; also termed B-cell chronic lymphocytic leukemia B-CLL), hairy cell leukemia and chronic myelogenous leukemia). Additional B-cell malignancies include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, grey zone lymphoma, B-cell proliferations of uncertain malignant potential, lymphomatoid granulomatosis, and post-transplant lymphoproliferative disorder. In addition, CD37-positive malignancies include, without limitation, T-cell lymphomas, multiple myelomas, and acute lymphocytic leukemias.

The CD37 antibody may be administered alone or in combination with adjuvants that enhance the stability, facilitate administration of pharmaceutic compositions containing them in certain embodiments, provide increased dissolution or dispersion, increase activity, provide adjunct therapy, and the like. Advantageously, such combinations may utilize lower dosages of the active ingredient, thus reducing possible toxicity and adverse side effects.

LEGEND TO SEQUENCE LISTING

Figure 1:
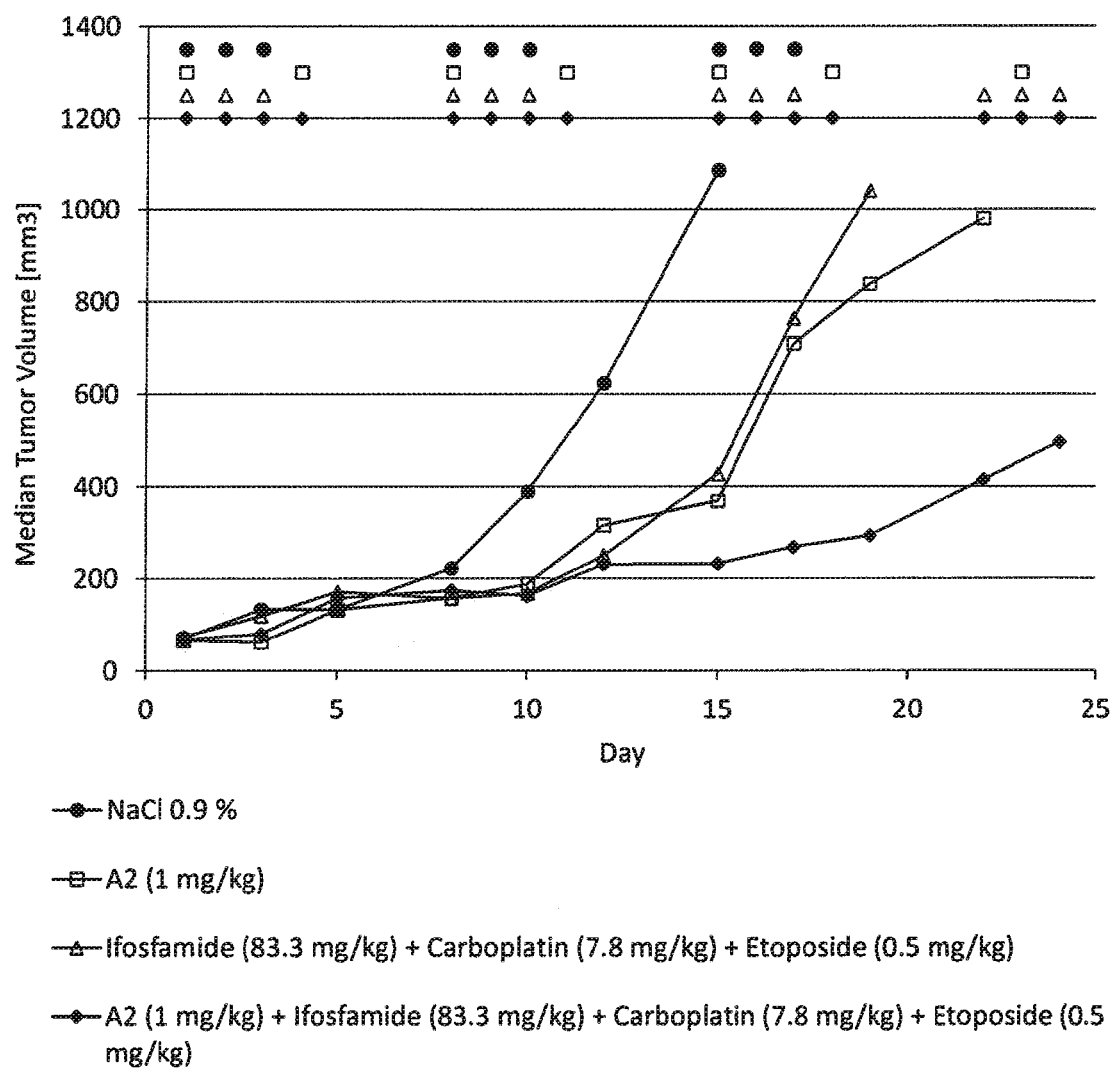
FIG. 1: Tumor growth kinetics of Ramos xenografts in vivo Ramos tumor-bearing mice are treated with mAb A2, ICE, or with the combination of ICE and mAb A2. Median tumor volumes of each treatment group are plotted over time. Day 1 is the first day, day 24 the last day of the experiment. Symbols indicate treatments; dosings are indicated in the figure legend.
Figure 2:
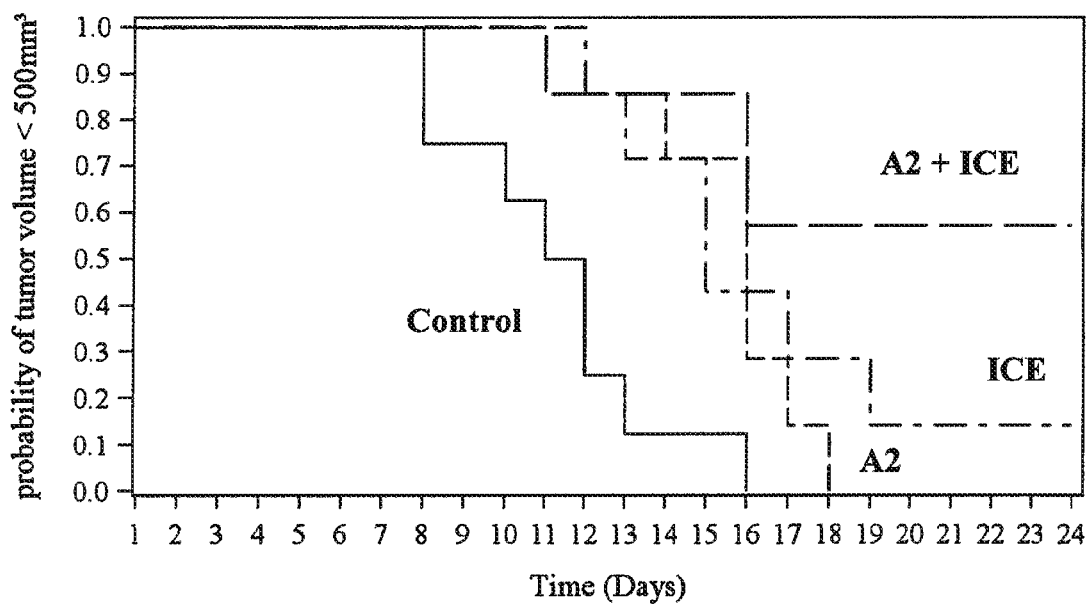
FIG. 2: Timepoint (day) when tumor volume exceeds 500 mm$^3$—probability curve Ramos tumor-bearing mice are treated with ICE, A2 or with the combination of ICE and A2. Probability curves are plotted over time. The curves indicate the probability of tumor volume not exceeding a volume of 500 mm$^3$. Individual treatment groups are indicated in the legend.

SEQ ID NO 1: nucleic acid sequence variable heavy (Vh) chain
SEQ ID NO 2: amino acid sequence variable heavy chain
SEQ ID NO 3: nucleic acid sequence variable light (Vl) chain
SEQ ID NO 4: amino acid sequence variable light chain
SEQ ID NO 5: A2 heavy chain amino acid sequence
SEQ ID NO 6: A2 light chain amino acid sequence
SEQ ID NO 7: constant heavy chain amino acid sequence
SEQ ID NO 8: constant light chain amino acid sequence
SEQ ID NO 9: A4 heavy chain amino acid sequence
SEQ ID NO 10: A4 light chain amino acid sequence
SEQ ID NO 11: B2 heavy chain amino acid sequence
SEQ ID NO 12: B2 light chain amino acid sequence
SEQ ID NO 13: B4 heavy chain amino acid sequence
SEQ ID NO 14: B4 light chain amino acid sequence
SEQ ID NO 15: CDR1 heavy chain (H1)
SEQ ID NO 16: CDR2 heavy chain (H2)
SEQ ID NO 17: CDR3 heavy chain (H3)
SEQ ID NO 18: CDR1 light chain (L1)
SEQ ID NO 19: CDR2 light chain (L2)
SEQ ID NO 20: CDR3 light chain (L3)
SEQ ID NO 21: alternative CDR2 heavy chain (H2b)

DETAILED DESCRIPTION OF THE INVENTION

In the present study, two cycles of combination therapy with ICE and A2 show improved efficacy (TGI=84%) compared to single-agent treatment. The mAb A2 administered as a single agent significantly inhibits growth of lymphomas (Ramos lymphomas). Addition of A2 to ICE chemotherapy improves efficacy, the combination is superior to single-agent A2. Improved efficacy of a combination of A2 and ICE chemotherapy is indicative for additive or synergistic effects of such a combination. An improved anti-tumor efficacy of a combination treatment of A2 and ICE provides a potential clinical benefit over monotherapy for patients suffering from CD37-positive malignancies.

In an in vivo SHO immunodeficient mouse model the combination of a CD37 antibody (such as mAb A2 or B2, preferably mAb A2) and ICE shows an improved anti-tumor effect over that of single agent treatment. These results show that a combination of a CD37 antibody (such as mAb A2 or B2, preferably mAb A2) with ICE results in superior anti-tumor efficacy compared to single agent treatment.

Definitions

Terms not specifically defined herein should be given the meanings that would be given to them by one of skill in the art in light of the disclosure and the context. The general embodiments "comprising" or "comprised" encompass the more specific embodiment "consisting of". Furthermore, singular and plural forms are not used in a limiting way. As used in the specification, however, unless specified to the contrary, the following terms have the meaning indicated and the following conventions are adhered to.

The term "ICE" describes a combination chemotherapy regimen employing three drugs: ifosfamide, carboplatin, and etoposide (or etoposide phosphate). This regimen is commonly used to treat recurrent lymphomas.

Ifosfamide is an alkylating agent used in the treatment of cancer. The chemical mass formula of Ifosfamide is $C_7H_{15}Cl_2N_2O_2P$ with a molecular mass of 261.1 g/mol. The systematic (IUPAC) name is N-3-bis(2-chloroethyl)-1,3,2-oxazaphosphinan-2-amide-2-oxide. The chemical structure of Ifosfamide is as follows:

(formula I)

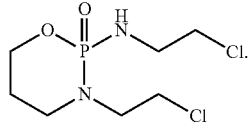

Carboplatin, or cis-Diammine(1,1-cyclobutanedicarboxylato)platinum(II) (trade names Paraplatin and Paraplatin-AQ) is a chemotherapy drug known to be an alkylating agent. The chemical mass formula of carboplatin is $C_6H_{12}N_2O_4Pt$ with a molecular mass of 371.249 g/mol. The systematic (IUPAC) name is cis-diammine(cyclobutane-1,1-dicarboxylate-O,O') platinum(II). The chemical structure of carboplatin is as follows:

(formula II)

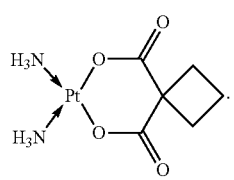

Etoposide phosphate (brand names: Eposin, Etopophos, Vepesid, VP-16) is a topoisomerase II inhibitor. The chemical mass formula of etoposide phosphate is $C_{29}H_{32}O_{13}$ with a molecular mass of 588.557 g/mol. The systematic (IUPAC) name is 4'-demethyl-epipodophyllotoxin 9-[4,6-O—(R)-ethylidene-beta-D-glucopyranoside], 4'-(dihydrogen phosphate). The chemical structure of etoposide phosphate is as follows:

(formula III)

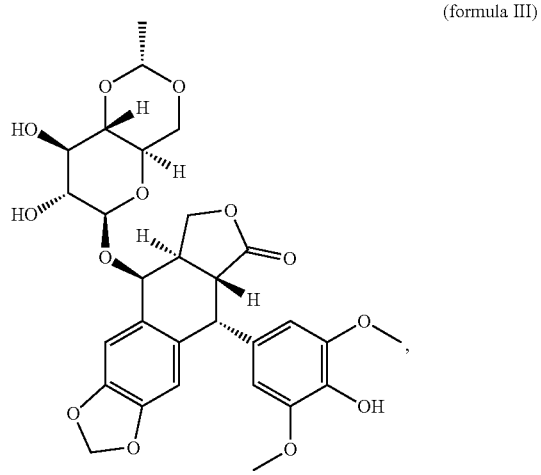

or with a phosphate group (formula IV)

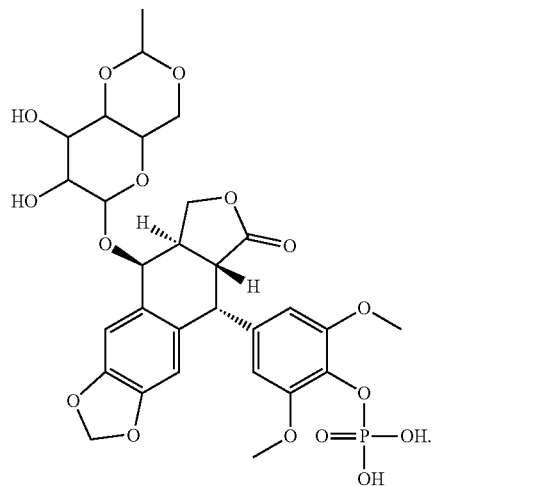

"Rituximab" is a chimeric monoclonal antibody against the protein CD20. The chemical mass formula of Rituximab is $C_{6416}H_{9874}N_{1688}O_{1987}S_{44}$ with a molecular mass of 143859.7 g/mol.

"CD37", a member of the tetraspanin superfamily, is a heavily glycosylated cell surface molecule with four transmembrane domains and two extracellular loops. CD37 is predominantly expressed on B cells and B-cell malignancies; low level expression of CD37 has been reported on T cells, granulocytes, and monocytes. High levels of CD37 expression have been observed in samples of patients with chronic lymphocytic leukemia (CLL) and different subtypes of non-Hodgkin's lymphoma (NHL) including mantle cell lymphoma (MCL) (Schwartz-Albiez et al, Journal Immunol 140: 905-914, 1988; Barrena et al., Leukemia 19: 1376-1383, 2005). This expression pattern makes CD37 an attractive target for antibody-mediated cancer therapy. Binding of a CD37-specific mAb to cancer cells may trigger various mechanisms of action: First, after the antibody binds to the extracellular domain of the CD37 antigen, it may activate the complement cascade and lyse the targeted cell. Second, an anti-CD37 antibody may mediate antibody-dependent cell-mediated cytotoxicity (ADCC) to the target cell, which occurs after the Fc portion of the bound antibody is recognized by appropriate receptors on cytotoxic cells of the immune system. Third, the antibody may alter the ability of B-cells to respond to antigen or other stimuli. Finally, anti-CD37 antibody may initiate programmed cell death (apoptosis).

"CD37 positive", "CD37 positive cells" or "CD37 positive malignancies" means that the detection of CD37 is possible/feasible by immunohistochemistry, flow cytometry such as FACS (fluorescence activated cell sorter) analysis (of e.g. blood, bone marrow or cell suspensions) or alternative techniques. Suitable assays to detect CD37 positive cells/malignancies are well known to a person skilled in the art.

The terms "CD37 antibody", "CD37 antibody molecule", "anti-CD37 antibody" and "anti-CD37 antibody molecule" as used in the present invention specifically relate to an antibody with a binding specificity for CD37 antigen. Examples of such antibodies are known in the art and are further described below.

The terms "anti-CD37 antibody molecule", "anti-CD37 antibody", "CD37 antibody" and "CD37 antibody molecule" are used interchangeably.

The term "CD37 antibody" or "anti-CD37 antibody molecule" encompasses anti-CD37 antibodies and anti-CD37 antibody fragments as well as conjugates with antibody molecules. Antibodies include, in the meaning of the present invention, chimeric monoclonal and humanized monoclonal antibodies. The term "antibody", which may interchangeably be used with "antibody molecule", shall encompass complete immunoglobulins (as they are produced by lymphocytes and for example present in blood sera), monoclonal antibodies secreted by hybridoma cell lines, polypeptides produced by recombinant expression in host cells, which have the binding specificity of immunoglobulins or monoclonal antibodies, and molecules which have been derived from such antibodies by modification or further processing while retaining their binding specificity.

In certain embodiments, the antibody molecule of the invention is a chimeric CD37-specific antibody that has the heavy chain variable region of a non-human antibody defined in a) or b) fused to the human heavy chain constant region IgG1 and the light chain variable region of a non-human antibody defined in a) or b) fused to the human light chain constant region kappa.

The CD37 antibody may also be in the form of a conjugate, i.e. an antibody molecule that is chemically coupled to a cytotoxic agent, particularly a cytotoxic agent that induces cytotoxicity (e.g. apoptosis or mitotic arrest) of tumor cells. As a result of normal pharmacologic clearance mechanisms, an antibody employed in a drug conjugate (an "immunoconjugate") contacts and binds to target cells only in limited amounts. Therefore, the cytotoxic agent employed in the conjugate must be highly cytotoxic such that sufficient cell killing occurs to elicit a therapeutic effect. As described in US 2004/0241174, examples of such cytotoxic agents include taxanes (see, e.g. WO 01/38318 and WO 03/097625), DNA-alkylating agents (e.g., CC-1065 analogs), anthracyclines, tubulysin analogs, duocarmycin analogs, doxorubicin, auristatin E, ricin A toxin, and cytotoxic agents comprising a reactive polyethylene glycol moiety (see, e.g., Sasse et al., 2000; Suzawa et al., 2000; Ichimura et al., 1991; Francisco et al., 2003; U.S. Pat. No. 5,475,092; U.S. Pat. No. 6,340,701; U.S. Pat. No. 6,372,738; and U.S. Pat. No. 6,436,931; US 2001/0036923; US 2004/0001838; US 2003/0199519; and WO 01/49698).

In a preferred embodiment, the cytotoxic agent is a maytansinoid, i.e. a derivative of maytansine (CAS 35846538), maytansinoids being known in the art to include maytansine, maytansinol, C-3 esters of maytansinol, and other maytansinol analogues and derivatives (see, e.g., U.S. Pat. No. 5,208, 020; and U.S. Pat. No. 6,441,163).

Anti-CD37 antibody immunoconjugates may be designed and synthesized as described in WO 2007/077173 for anti-FAP immunoconjugates.

In a further embodiment, the anti-CD37 molecule of the invention may be radioactively labelled to form a radioimmunoconjugate, an approach suggested for the anti-CD37 antibody MB-1 (Buchsbaum et al., 1992, see above). Radionuclides with advantageous radiation properties are known in the art, examples are Phosphorus-32, Strontium-89, Yttrium-90, Iodine-131, Samarium-153, Erbium-169, Ytterbium-175, Rhenium-188, that have been successfully and stably coupled to MAbs. The CD37 antibodies of the invention may be labelled with various radionuclides using direct labelling or indirect labelling methods known in the art, as described in U.S. Pat. No. 6,241,961. A review on technologies for generating and applying novel radiolabeled antibody conjugates that are useful in the present invention, is given by Goldenberg and Sharkey, 2007.

An antibody molecule of the invention, whether Fc-engineered or not, may also be bispecific, i.e. an antibody molecule that binds to two different targets, one of them being CD37, the other one being selected from e.g. surface antigens expressed by T cells, e.g. CD3, CD16 and CD56.

The term "antibody" or "antibodies" comprises monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments. The term "antibody" or "antibodies" comprises antibodies of human or non-human origin, humanised as well as chimeric antibodies and furthermore Fc-engineered antibodies or Fc-fusion molecules. Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cysteine groups of the constant chains is not possible in these Fv fragments, they are often stabilised by some other method. For this purpose the variable regions of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known in the art.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia, tri- and pentabodies).

The term "diabody" is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphite bridges. Examples of diabodies can be found in the literature.

The term "minibody" is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are known in the art.

The term "triabody" is used in the art to denote a trivalent homotrimeric scFv derivative. The direct fusion of VH-VL without the use of a linker sequence leads to the formation of trimers.

The fragments known in the art as mini antibodies which have a bi, tri- or tetravalent structure are also derivatives of scFv fragments. The multimerisation is achieved by means of di-, tri- or tetrameric coiled coil structures.

There are also "scaffold proteins" or "scaffold antibodies" known in the art. Using this term, a scaffold protein means any functional domain of a protein, especially an antibody that is coupled by genetic cloning or by co-translational processes with another protein or part of a protein that has another function.

The term "Complementary determining region" or "CDR" or "CDRs" of an antibody/antibody molecule means the hypervariable regions (also called Complementarity Determining Regions, abbreviated to "CDRs") of immunoglobulins. The CDRs were originally defined by Kabat et al., ("Sequences of Proteins of Immunological Interest" Kabat, E., of al., U.S. Department of Health and Human Services, (1983) and Kabat E. A., Wu T. T., Perry H. M., Gottesman K. S. and Foeller C. Sequences of Proteins of Immunological Interest (5th Ed.). NIH Publication No. 91-3242. U.S. Department of Health and Human Services, Public Health Service, National Institutes of Health, Bethesda, Md. 1991) based on extent of sequence variability of numerous antibody sequences. The CDRs are believed to contact the target antigen of an antibody and to be primarily responsible for binding. Chothia et al (Chothia and Lesk, J. Mol. Biol., 196:901-917 (1987)) have given an alternate definition of the hypervariable regions or CDRs. The Chothia definition is based on the residues that constitute the loops in the 3-dimensional structures of antibodies.

In the specific context of the present invention the CDRs are determined on the basis of the Kabat system. From the sequences of the variable regions as shown in SEQ ID NO: 2 and SEQ ID NO: 4, the CDR sequence can be routinely determined by searching the Kabat sequence database for sequence features. The 3 CDRs contained within the variable heavy chain as shown in SEQ ID NO:2 comprise preferably positions 31-35 (H1, SEQ ID NO: 15), 50-66 (H2, SEQ ID NO: 16) or 50-62 (H2b, SEQ ID NO: 21) and 99-105 (H3, SEQ ID NO: 17), the 3 CDRs contained within the variable light chain as shown in SEQ ID NO:4 comprise preferably positions 24-34 (L1, SEQ ID NO: 18), 50-56 (L2, SEQ ID NO: 19) and 89-97 (L3, SEQ ID NO: 20).

The term "treatment cycle" describes a time period of between 1 to 6 weeks, preferably 2 to 4 weeks, most preferably 3 weeks, wherein the patient receives at least one dose of the CD37 antibody and at least one dose of ICE.

The terms "dose" and "dosage" are used interchangeably.
The terms "NHL" and "B-NHL" are used interchangeably.

Embodiments

The present invention concerns a CD37 antibody for use in a method for the treatment of a patient suffering from a CD37-positive malignancy, preferably a B-cell malignancy, most preferably chronic lymphocytic leukemia (CLL) or B-cell non-Hodgkin's lymphoma (B-NHL), in combination with ICE (=a combination chemotherapy regimen employing three drugs: ifosfamide, carboplatin, and etoposide (or etoposide phosphate)), whereby the CD37 antibody comprises:
  a) a variable heavy chain comprising CDRs having the SEQ ID NOs: 15, 16 or 21, and 17, and
  b) a variable light chain comprising CDRs having the SEQ ID NOs: 18, 19 and 20.

The present invention further concerns a CD37 antibody for use in a method for the treatment of a patient suffering from a CD37-positive malignancy, preferably a B-cell malignancy, most preferably chronic lymphocytic leukemia (CLL) or B-cell non-Hodgkin's lymphoma (B-NHL), in combination with ICE and a CD20 antibody like Rituximab (called R-ICE), whereby the CD37 antibody comprises:
  a) a variable heavy chain comprising CDRs have the SEQ ID NOs: 15, 16 or 21, and 17, and
  b) a variable light chain comprising CDRs having the SEQ ID NOs: 18, 19 and 20.

The present invention furthermore concerns a CD37 antibody for use in a method for the treatment of a patient suffering from a CD37-positive malignancy, preferably a B-cell malignancy, most preferably chronic lymphocytic leukemia (CLL) or B-cell non-Hodgkin's lymphoma (B-NHL), in combination with a chemotherapeutic agent (such as e.g. an alkylating agent) and a CD20 antibody like Rituximab (called R-chemotherapy), whereby the CD37 antibody comprises:
  a) a variable heavy chain comprising CDRs having the SEQ ID NOs: 15, 16 or 21, and 17, and
  b) a variable light chain comprising CDRs having the SEQ ID NOs: 18, 19 and 20.

In a specific embodiment the CD37 antibody is a chimeric antibody. Preferably said chimeric antibody comprises the human constant heavy chain amino acid sequence SEQ ID NO:7 and the human constant light chain amino acid sequence SEQ ID NO:8.

In a preferred embodiment the CD37 antibody comprises the heavy chain amino acid sequence SEQ ID NO: 5 and the light chain amino acid sequence SEQ ID NO: 6 (=>A2).

In a specific embodiment the CD37 antibody is a humanized antibody. Preferably said humanized CD37 antibody comprises the heavy chain amino acid sequence SEQ ID NO: 11 and the light chain amino acid sequence 12 (=>B2).

In a specific embodiment the patient receives at least one dose of the CD37 antibody and at least one administration of ICE during a treatment cycle, whereby a treatment cycle is a time period of about 1 to 6 weeks, preferably 2 to 4 weeks, most preferably 3 weeks.

In a further specific embodiment the CD37 antibody is administered to the patient simultaneously with the administration of ICE.

In another embodiment the CD37 antibody is administered to the patient after the administration of ICE, preferably within 24 hrs or within 36 hrs after the administration of ICE.

In a further embodiment the CD37 antibody is administered to the patient before the administration of ICE, preferably within 24 hrs or within 36 hrs before the administration of ICE.

In another preferred embodiment the CD37 antibody is administered to the patient after a 3 day consecutive application of ICE, preferably within 24 hrs or within 36 hrs after the administration of the last ICE dosage (which is usually etoposide on day 3). Preferably ICE is administered to the patient on days 1, 2 and 3 of a 1 to 6 week treatment cycle, more preferably of a 2-4 week treatment cycle, most preferably of a 3 week treatment cycle, and the CD37 antibody is administered on day 3 after the last ICE administration or on day 4 of the treatment cycle or several days after the 3 consecutive ICE treatment days.

In a further preferred embodiment the CD37 antibody is administered to the patient before a 3 day consecutive application of ICE, preferably within 24 hrs or within 36 hrs before the administration of the first ICE dosage (which is usually ifosfamide). Preferably CD37 antibody is administered on day 1 of the treatment cycle and ICE is administered to the patient on days 2, 3, and 4 of a 1 to 6 week treatment cycle, more preferably of a 2-4 week treatment cycle, most preferably of a 3 week treatment cycle.

In a specific embodiment the CD37 antibody is additionally administered at least one more time in between, preferably in the middle of the treatment cycle at about 1-2 weeks or 1.5 weeks.

In another embodiment the CD37 antibody is additionally administered once weekly. The treatment cycle is a time period of between 1 to 6 weeks, preferably 2 to 4 weeks, most preferably 3 weeks, wherein the patient receives at least one dose of the CD37 antibody and at least one dose of ICE.

The CD37 antibody, preferably A2 (CD37 antibody comprising SEQ ID NOs: 5 and 6) and B2 (CD37 antibody comprising SEQ ID NOs: 11 and 12), most preferably A2, is administered in a dose of about 0.01 µg/kg to 40 mg/kg or in a dose of about 10 µg/kg to 40 mg/kg or in a dose of about 1 mg and 2800 mg per patient. Administration to the patient may occur by one or more separate administrations. It may occur for example by infusion such as continuous infusion.

For A2 (CD37 antibody comprising SEQ ID Nos:5 and 6), the estimated dose for a 70 kg human is in the range of 1 mg to 2800 mg, preferably 1 mg to 1400 mg, or 10 mg to 1400 mg, or 10 mg to 1000 mg, or 100 mg to 1400 mg, or 100 mg to 385 mg, most preferably 10 mg to 1400 mg. Said dose is preferably a weekly dose. A dose range of 1 mg to 2800 mg or 2 mg to 800 mg or more specifically 200 mg to 770 mg for a 70 kg human is preferred, if A2 is administered every two weeks. The estimated human dose of B2 (CD37 antibody comprising SEQ ID Nos:11 and 12) for a 70 kg human is in the range of 1 mg to 2800 mg, preferably in the range of 1 mg to 1400 mg or 10 mg to 1400 mg, or 10 mg to 1000 mg, or 100 mg to 1400 mg, or more specifically 100 mg to 385 mg. Said dose is preferably a weekly dose. A dose range of 1 mg to 2800 mg or 2 mg to 800 mg or more specifically 200 mg to 770 mg for a 70 kg human is preferred, if B2 is administered every two weeks.

ICE is preferably administered on three consecutive days of a treatment cycle, which is preferably 2-3 weeks (14-21 days) long, most preferably 3 weeks (21 days) long.

Preferably the doses of each component of ICE range:
i) for ifosfamide between 3-7 g/m$^2$ body surface, preferably the ifosfamide dose is 5 g/m$^2$, preferably ifosfamide is administered on the 2$^{nd}$ treatment day,
ii) for carboplatin between 200-800 mg (dose is based on clearance and area under curve (AUC)), preferably carboplatin is administered on the 2$^{nd}$ treatment day and
iii) for etoposide between 50-200 mg/m$^2$, preferably the etoposide dose is 100 mg/m$^2$, preferably etoposide is administered on the 1$^{st}$, 2$^{nd}$ and 3$^{rd}$ treatment day.

The ICE dose as described above is administered preferably on days 1, 2 and 3 of a 2-3 week treatment cycle. Furthermore, preferred is the administration of ICE dosing as described above on 3 consecutive days following a CD37 antibody administration (e.g. day 1=CD37 administration in any of the dosages as described above, days 2+3+4=ICE administration in any of the dosages as described above) of a preferably 2-3 week long treatment cycle.

The ICE dosing may be administered by any way, e.g. infusion, parenteral or oral administration.

The CD37 antibody dose may be administered by any way, e.g. infusion such as continuous infusion, subcutaneous injection, inhalation, parenteral or oral administration.

In a specific embodiment of the present in invention a CD37 antibody is administered in combination with ICE as first line treatment. First line treatment means as a first treatment option (before other treatment options are performed/used).

In a preferred embodiment of the present in invention a CD37 antibody is administered in combination with ICE as second line treatment of CLL or B-NHL.

In another specific embodiment of the present in invention a CD37 antibody is administered in combination with ICE as second line or third or fourth or further line treatment. Second, third, fourth or further line treatment means the administration as a second, third, fourth or later/further line treatment option after one or more other treatment(s) already has (have) been performed/used.

For the treatment of a patient suffering from NHL a preferred treatment cycle scheme lasts for a time period of 2-4 weeks, whereby ICE is preferably administered on days 1 to 3 and whereby at least one CD37 antibody, preferably A2 or B2, is administered at a dose as described above either before, after or simultaneously with the ICE administration. Simultaneously hereby means on the same day(s). Furthermore, another preferred treatment cycle scheme for NHL comprises additional administration(s) of CD37 antibody inbetween, for example once a week, thus resulting in several, preferably 2 to 4, most preferably 3 administrations of CD37 antibody per treatment cycle.

In a specific embodiment of the present invention any of the described treatment cycle schemes for ICE as described in the paragraphs above is combined with the administration of an antibody targeting CD20 such as Rituximab. This treatment option is referred to as R-ICE.

In a preferred embodiment of the present invention any of the described treatment cycle schemes for ICE+CD37 mAb as described in the paragraphs above is combined with the administration of an antibody targeting CD20 such as Rituximab. This treatment option is referred to as R-ICE+CD37 mAb.

In a preferred treatment cycle scheme for R-ICE the Rituximab (or alternatively any other antibody targeting CD20) is embedded into the ICE treatment cycle and dosing scheme (dosing as described in the paragraphs above), preferably by administering the antibody targeting CD20 (e.g. Rituximab) together with etoposide on the 1$^{st}$ treatment day. A preferred dose for Rituximab is 100-500 mg/m² body surface, preferably 375-500 mg/m², most preferably 375 mg/m².

For CD37 combination therapy during a R-ICE treatment cycle at least one CD37 antibody, preferably A2 or B2, is administered at a dose as described above either before, after, or simultaneously with the R-ICE administration. Simultaneously hereby means on the same day(s). Furthermore, another preferred treatment cycle scheme for NHL comprises additional administration(s) of CD37 antibody in-between, for example in the middle of the treatment cycle at about 1-2 weeks, preferably 1.5 weeks.

The present invention further concerns a method of reducing CD37-positive cells, more specifically B-cells, comprising exposing B-cells to a combination of a CD37 antibody and ICE or R-ICE, whereby said CD37 antibody comprises:
 a) a variable heavy chain comprising CDRs have the SEQ ID NOs: 15, 16 or 21, and 17, and
 b) a variable light chain comprising CDRs having the SEQ ID NOs: 18, 19 and 20.

The present invention further concerns a method of reducing CD37-positive cells, more specifically B-cells, comprising exposing B-cells to a combination of a CD37 antibody, a chemotherapeutic agent such as e.g. an alkylating agent and a CD20 antibody such as
 Rituximab, whereby said CD37 antibody comprises:
 a) a variable heavy chain comprising CDRs have the SEQ ID NOs: 15, 16 or 21, and 17, and
 b) a variable light chain comprising CDRs having the SEQ ID NOs: 18, 19 and 20.

The present invention furthermore concerns a method of depleting CD37 expressing B-cells from a population of cells comprising administering to said population of cells: a) a CD37 antibody or a pharmaceutical composition comprising a CD37 antibody and b) ICE or R-ICE, wherein said method is preferably carried out in vitro, and whereby said CD37 antibody comprises:
 a) a variable heavy chain comprising CDRs have the SEQ ID NOs: 15, 16 or 21, and 17, and
 b) a variable light chain comprising CDRs having the SEQ ID NOs: 18, 19 and 20.

The present invention further concerns a method of reducing CD37-positive cells comprising:
 a) Exposing CD37-positive cells to a CD37 antibody and
 b) Exposing CD37-positive cells to ICE or R-ICE,
 whereby said CD37 antibody of step a) comprises:
 i) a variable heavy chain comprising CDRs have the SEQ ID NOs: 15, 16 or 21, and 17, and
 ii) a variable light chain comprising CDRs having the SEQ ID NOs: 18, 19 and 20.

The present invention additionally concerns a method of reducing CD37-positive cells comprising:
 a) Exposing CD37-positive cells to a CD37 antibody, and
 b) Exposing CD37-positive cells to a chemotherapeutic agent such as e.g. an alkylating agent, and
 c) Exposing CD37-positive cells to a CD20 antibody such as Rituximab,
 whereby said CD37 antibody of step a) comprises:
 i) a variable heavy chain comprising CDRs have the SEQ ID NOs: 15, 16 or 21, and 17, and
 ii) a variable light chain comprising CDRs having the SEQ ID NOs: 18, 19 and 20.

The present invention furthermore concerns a method of reducing B-cells comprising:
 a) Exposing B-cells to a CD37 antibody and
 b) Exposing B-cells to ICE or R-ICE,
 whereby said CD37 antibody of step a) comprises:
 i) a variable heavy chain comprising CDRs have the SEQ ID NOs: 15, 16 or 21, and 17, and
 ii) a variable light chain comprising CDRs having the SEQ ID NOs: 18, 19 and 20.

In a specific embodiment the CD37 antibody is a chimeric antibody. Preferably said chimeric antibody comprises the human constant heavy chain amino acid sequence SEQ ID NO:7 and the human constant light chain amino acid sequence SEQ ID NO:8.

In a preferred embodiment the CD37 antibody comprises the heavy chain amino acid sequence SEQ ID NO: 5 and the light chain amino acid sequence SEQ ID NO: 6 (=>A2).

In a specific embodiment the CD37 antibody is a humanized antibody. Preferably said humanized CD37 antibody comprises the heavy chain amino acid sequence SEQ ID NO: 11 and the light chain amino acid sequence 12 (=>B2).

In a specific embodiment of any of said methods the CD37-positive cells are exposed to the CD37 antibody and ICE simultaneously. Said CD37-positive cells are preferably B-cells.

In another embodiment of any of said methods the CD37-positive cells are exposed to the CD37 antibody after they are exposed to ICE, preferably within 24 hrs or within 36 hrs after they are exposed to ICE. Said CD37-positive cells are preferably B-cells.

In a further embodiment of any of said methods the CD37-positive cells are exposed to the CD37 antibody before they are exposed to ICE, preferably within 24 hrs or within 36 hrs before they are exposed to ICE. Said CD37-positive cells are preferably B-cells.

In a specific embodiment said method is carried out in vivo.
In a specific embodiment said method is carried out in vitro.

The present invention further concerns a kit for reducing CD37-positive cells comprising:
 a) a container comprising a CD37 antibody, whereby said CD37 antibody comprises:
  i) a variable heavy chain comprising CDRs having the SEQ ID NOs: 15, 16 or 21, and 17, and
  ii) a variable light chain comprising CDRs having the SEQ ID NOs: 18, 19 and 20, and
 b) a protocol for using the kit to reduce CD37-positive cells (by administration of the CD37 antibody of step a) in combination with a chemotherapeutic agent/treatment such as ICE or R-ICE. Said CD37-positive cells are preferably B-cells.

The present invention specifically concerns a kit for reducing CD37-positive cells comprising:
 a) a container comprising a CD37 antibody, whereby said CD37 antibody comprises:
  i) a variable heavy chain comprising CDRs having the SEQ ID NOs: 15, 16 or 21, and 17, and
  ii) a variable light chain comprising CDRs having the SEQ ID NOs: 18, 19 and 20, and
 b) a protocol for using the kit to reduce CD37-positive cells by administration of the CD37 antibody of step a) in combination with ICE and/or
 c) optionally a protocol for using the kit to reduce CD37-positive cells by administration of the CD37 antibody of step a) in combination with ICE and a CD20 antibody such as Rituximab.

The present invention furthermore concerns a kit for reducing CD37-positive cells comprising:
 a) a first container comprising a CD37 antibody, whereby said CD37 antibody comprises:

i) a variable heavy chain comprising CDRs have the SEQ ID NOs: 15, 16 or 21, and 17, and
ii) a variable light chain comprising CDRs having the SEQ ID NOs: 18, 19 and 20, and b) a second container comprising a chemotherapeutic agent/treatment such as ICE, and
c) optionally a third container comprising a CD20 antibody like Rituximab, and
d) a protocol for using the kit to reduce CD37-positive cells. Said CD37-positive cells are preferably B-cells.

In a specific embodiment the protocol in step c) indicates to administer the CD37 antibody and ICE or R-ICE simultaneously.

In another embodiment the protocol in step c) indicates to administer the CD37 antibody before ICE or R-ICE, preferably within 24 hrs or within 36 hrs before the administration of ICE or R-ICE.

In a further embodiment the protocol in step c) indicates to administer the CD37 antibody after ICE or R-ICE, preferably within 24 hrs or within 36 hrs after the administration of ICE or R-ICE.

In a specific embodiment the protocol in step c) indicates to administer the kit components to a patient suffering from a CD37-positive malignancy, preferably a B-cell malignancy, preferably chronic lymphocytic leukemia (CLL) or NHL, most preferably CLL.

In a further specific embodiment the protocol in step c) indicates that the patient receives at least one dose of the CD37 antibody and at least one dose of ICE or R-ICE during a treatment cycle, whereby a treatment cycle is a time period of about 1 to 6 weeks, preferably 2 to 4 weeks, most preferably 3 weeks.

In further specific embodiments the protocol in step c) indicates treatment cycles and/or dosage schemes as described above for the second medical use of the described CD37 antibodies.

The present invention further concerns an article of manufacture comprising a CD37 antibody and a chemotherapeutic agent/treatment such as ICE or R-ICE and a label indicating a method as described above, whereby the CD37 antibody comprises: a) a variable heavy chain comprising CDRs have the SEQ ID NOs: 15, 16 or 21, and 17, and b) a variable light chain comprising CDRs having the SEQ ID NOs: 18, 19 and 20.

The present invention furthermore concerns a pharmaceutical composition comprising, a CD37 antibody, ICE or R-ICE, and a pharmaceutically acceptable carrier, whereby the CD37 antibody comprises:
a) a variable heavy chain comprising CDRs have the SEQ ID NOs: 15, 16 or 21, and 17, and
b) a variable light chain comprising CDRs having the SEQ ID NOs: 18, 19 and 20.

In a specific embodiment the pharmaceutical composition comprises as the active ingredient a CD37 antibody and ICE, and additionally a pharmaceutically acceptable carrier, whereby the CD37 antibody comprises:
a) The CDRs contained within the variable heavy chain as shown in SEQ ID NO:2, preferably said CDRs have SEQ ID NOs: 15, 16 or 21, and 17, and
b) The CDRs contained within the variable light chain as shown in SEQ ID NO:4, preferably said CDRs have SEQ ID NOs: 18, 19 and 20.

The present invention further concerns the pharmaceutical composition as described above for use as a medicament.

The present invention furthermore concerns the pharmaceutical composition as described above for use in a method for the treatment of a patient suffering from a B-cell malignancy, preferably for use in a method for the treatment of a B-cell non Hodgkin's lymphoma (B-NHL) or a chronic lymphocytic leukemia (CLL) patient.

The present invention further concerns a method of treating a B-cell malignancy comprising administering a therapeutically effective amount of a CD37 antibody in combination with ICE or R-ICE to a patient in need thereof, whereby the CD37 antibody comprises:
a) a variable heavy chain comprising CDRs have the SEQ ID NOs: 15, 16 or 21, and 17, and
b) a variable light chain comprising CDRs having the SEQ ID NOs: 18, 19 and 20.

The present invention additionally concerns a method of treating a B-cell malignancy comprising administering a therapeutically effective amount of a CD37 antibody in combination with a chemotherapeutic agent/treatment and a CD20 antibody like Rituximab to a patient in need thereof, whereby the CD37 antibody comprises:
a) a variable heavy chain comprising CDRs have the SEQ ID NOs: 15, 16 or 21, and 17, and
b) a variable light chain comprising CDRs having the SEQ ID NOs: 18, 19 and 20.

The present invention furthermore concerns a method for treating a patient suffering from a B-cell malignancy selected from B-cell non-Hodgkin's lymphoma, B-cell chronic lymphocytic leukemia and multiple myeloma, comprising administering to said patient an effective amount of a pharmaceutical composition of the present invention.

The present invention further concerns a method of treating a B-cell malignancy comprising administrating a therapeutically effective amount of a) A CD37 antibody and b) ICE or R-ICE, to a patient in need thereof, whereby the CD37 antibody comprises:
a) a variable heavy chain comprising CDRs have the SEQ ID NOs: 15, 16 or 21, and 17, and
b) a variable light chain comprising CDRs having the SEQ ID NOs: 18, 19 and 20.

In a specific embodiment of said methods of treatment the patient receives at least one dose of the CD37 antibody and at least one dose of ICE or R-ICE during a treatment cycle, whereby a treatment cycle is a time period of about 1 to 6 weeks, preferably 2 to 4 weeks, most preferably 3 weeks.

In a specific embodiment of any of said methods the B-cells are exposed to the CD37 antibody and ICE or R-ICE simultaneously.

In another embodiment of any of said methods the B-cells are exposed to the CD37 antibody after they are exposed to ICE or R-ICE, preferably within 24 hrs or within 36 hrs after they are exposed to ICE or R-ICE.

In a further embodiment of any of said methods the B-cells are exposed to the CD37 antibody before they are exposed to ICE or R-ICE, preferably within 24 hrs or within 36 hrs before they are exposed to ICE or R-ICE.

In a specific embodiment said method is carried out in vivo.
In a specific embodiment said method is carried out in vitro.

The dosage regimens described above for the second medical use of CD37 antibodies in combination with ICE or R-ICE likewise apply for the described methods of treatment of the present invention.

The present invention further concerns the CD37 antibody as described, any of the methods as described, the kit as described, the article of manufacture as described, the pharmaceutical composition as described, and the methods of treatment as described, whereby the CD37 antibody is a chimeric antibody defined by a) a variable heavy chain comprising the amino acid sequence shown in SEQ ID NO: 2, and b) a variable light chain comprising the amino acid sequence shown in SEQ ID NO: 4, whereby the constant heavy and light chains are preferably of human origin.

The present invention furthermore concerns the CD37 antibody as described, any of the methods as described, the kit as described, the article of manufacture as described, the pharmaceutical composition as described, and the methods of treatment as described, whereby the antibody has a heavy chain comprising the amino acid sequence of SEQ ID NO: 5 and a light chain comprising the amino acid sequence of SEQ ID NO: 6.

The present invention furthermore concerns the CD37 antibody as described, any of the methods as described, the kit as described, the article of manufacture as described, the pharmaceutical composition as described, and the methods of treatment as described, the antibody has a heavy chain comprising the amino acid sequence of SEQ ID NO: 7 fused to SEQ ID NO: 2 and a light chain comprising the amino acid sequence of SEQ ID NO: 8 fused to SEQ ID NO: 4.

The present invention furthermore concerns the CD37 antibody as described, any of the methods as described, the kit as described, the article of manufacture as described, the pharmaceutical composition as described, and the methods of treatment as described, whereby the antibody has a heavy chain comprising the amino acid sequence of SEQ ID NO: 9 and a light chain comprising the amino acid sequence of SEQ ID NO: 10.

The present invention furthermore concerns the CD37 antibody as described, any of the methods as described, the kit as described, the article of manufacture as described, the pharmaceutical composition as described, and the methods of treatment as described, whereby said antibody is a humanized antibody defined by frameworks supporting said CDRs that are derived from a human antibody, and wherein the constant heavy and light chains are from a human antibody.

The present invention furthermore concerns the CD37 antibody as described, any of the methods as described, the kit as described, the article of manufacture as described, the pharmaceutical composition as described, and the methods of treatment as described, whereby the antibody has a heavy chain comprising the amino acid sequence of SEQ ID NO: 11 and a light chain comprising the amino acid sequence of SEQ ID NO: 12.

The present invention furthermore concerns the CD37 antibody as described, any of the methods as described, the kit as described, the article of manufacture as described, the pharmaceutical composition as described, and the methods of treatment as described, whereby the antibody has a heavy chain comprising the amino acid sequence of SEQ ID NO: 13 and a light chain comprising the amino acid sequence of SEQ ID NO: 14.

The present invention furthermore concerns the CD37 antibody as described, any of the methods as described, the kit as described, the article of manufacture as described, the pharmaceutical composition as described, and the methods of treatment as described, whereby the CD37-positive malignancy is selected from the group consisting of: B-cell lymphomas, aggressive B-cell lymphoma, Hodgkin's disease, B-cell non-Hodgkin's lymphoma (NHL), lymphomas, Waldenström's macroglobulinaemia (also called lymphoplasmacytic lymphoma or immunocytoma), central nervous system lymphomas, leukemias, acute lymphoblastic leukemia (ALL), chronic lymphocytic leukemia (CLL; also termed B-cell chronic lymphocytic leukemia BCLL), hairy cell leukemia, chronic myoblastic leukemia, myelomas, multiple myeloma, T-cell lymphoma, small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, grey zone lymphoma, B-cell proliferations of uncertain malignant potential, lymphomatoid granulomatosis, and post-transplant lymphoproliferative disorder, whereby the CD37-positive malignancy is preferably a B-cell malignancy, preferably B-cell non-Hodgkin's lymphoma, B-cell chronic lymphocytic leukemia, whereby the B-cell malignancy is most preferably chronic lymphocytic leukemia (CLL).

The practice of the present invention will employ, unless otherwise indicated, conventional techniques of medicine, pharmacy, chemistry, biology, oncology, cell biology, molecular biology, cell culture, immunology and the like which are in the skill of one in the art. These techniques are fully disclosed in the current literature.

The following examples are not limiting. They merely show possible embodiments of the invention. A person skilled in the art could easily adjust the conditions to apply it to other embodiments.

EXPERIMENTAL

Materials and Methods

Antibodies and Reagents

Antibody A2 is expressed in DHFR-deficient Chinese hamster ovary (CHO) DG44 suspension cells under serum-free conditions and purified via MabSelect Protein A affinity chromatography (GE Healthcare). The antibody is formulated in citrate buffer at a concentration of 10 mg/ml and stored between 4° and 8° C. Holoxan® (ifosfamide, 40 mg/ml) is purchased from Baxter Oncology GmbH (Halle, Germany), carboplatin "EBEWE"® (10 mg/ml) and etoposide "EBEWE"® (2 mg/ml) from EBEWE Arzneimittel GmbH (Unterach, Austria). Ifosfamide (dissolved in sterile water), carboplatin (dissolved in 0.9% saline) and etoposide (dissolved in 0.9% saline) are mixed, diluted with 0.9% saline and administered as a cocktail ("ICE").

In Vivo Tumormodel

Mice are 11 week-old female Crl:SHO-PrkdcscidHrhr purchased from Charles River. After arrival, mice are allowed to adjust to ambient conditions for at least 5 days before they are used for the experiments. They are housed in Makrolon type III cages in groups of 7 (8 for the controls) under standardized conditions at 21.5+/−1.5° C. temperature and 55+/−10% humidity. Standardized diet (PROVIMI KLIBA) and autoclaved tap water were provided ad libitum. Subcutaneously implanted (under isoflurane anesthesia) microchips are used to identify each mouse. Cage cards showing the study number, the animal identification number, the compound and dose level, the administration route as well as the schedule remain with the animals throughout the study.

To establish subcutaneous tumors, Ramos (ATCC #CRL-1596) cells are harvested by centrifugation, washed and resuspended in PBS+5 FCS at $5 \times 10^7$ cells/ml. 100 µl cell suspension containing $5 \times 0^6$ cells is then injected subcutaneously into the right flank of the mice (1 site per mouse). Mice were randomly distributed between the treatment and the vehicle control group (13 days after cell injection) when tumors are well established and had reached diameters of 3 to 8 mm.

Tumor diameters are measured three times a week (Monday, Wednesday and Friday) with a caliper. The volume of each tumor [in mm$^3$] is calculated according to the formula "tumor volume=length*diameter$^2$*π/6." To monitor side effects of treatment, mice are inspected daily for abnormalities and body weight is determined three times a week (Monday, Wednesday and Friday) Animals are sacrificed when the control tumors reached a size of approximately 1000 mm$^3$ on average. In addition, animals with tumor sizes exceeding 1.5 cm in diameter or 20% body weight loss are euthanized for ethical reasons.

TGI (tumor growth inhibition) values are calculated as follows:

$$TGI=100\times\{1-[(treated_{final\ day}-treated_{day\ 1})/(control_{final\ day}-control_{day\ 1})]\}$$

Statistical Analysis

The statistical evaluation is performed for the parameters tumor volume and body weight at day 15. For the tumor volume absolute values and for the body weight the percentage change referred to the initial weight of day 1 is used. Due to the observed variation nonparametric methods are applied. For descriptive considerations the number of observations, the median, the minimum and the maximum are calculated. For a quick overview of possible treatment effects the median of the tumor volume of each treatment group T is referred to the median of the control C as Tumor growth inhibition (TGI) from day 1 until day $d$: $TGI=100*[(C_d-C_1)-(T_d-T_1)]/(C_d-C_1)$ where $C_1$, $T_1$=median tumor volumes in control and treatment group at start of the experiment at day 1, $C_d$, $T_d$=median tumor volumes in control and treatment group at day 15.

One-sided decreasing Wilcoxon tests are applied to compare each treatment group with the control, as well as the mono therapies with the corresponding combination therapy, looking for a reduction in tumor volume as effect and a reduction in the body weight gain as adverse event.

The same comparisons as for the tumor volume and the body weight are composed for the time points until the tumor volume exceeded 500 mm$^3$ The time point is determined by means of linear interpolation between the last time point with a tumor volume less than and the first time point with a volume greater than the defined value. Here a logrank test is applied. In the case that a tumor does not exceed the defined volume until the end of the experiment or the death of the animal the last observed time point is included in the analysis as a censored observation.

For each treatment group the median is calculated and referred to the median of the control group as an estimate for the delay A achieved by the corresponding therapy.

The p values for the tumor volume as well as for the time points of exceeding the predefined critical tumor volume (efficacy parameters) are adjusted for multiple comparisons according to Bonferroni-Holm within each subtopic (comparisons versus control, comparisons mono therapies versus combination therapy) whereas the p values of the body weight (tolerability parameter) remain unadjusted in order not to overlook a possible adverse effect.

The level of significance is fixed at α=5%. An (adjusted) p value of less than 0.05 is considered to show a statistically significant difference between the groups and differences are seen as indicative whenever 0.05≤p value <0.10.

The statistical evaluation is prepared using the software package SAS version 9.2 (SAS Institute Inc., Cary N.C., USA) and Proc StatXact version 8.0 (Cytel Software Corporation, Cambridge Mass., USA).

EXAMPLES

Example 1

Anti-Tumor Effect of mAB A2 in Combination with Ice in a Human Xenograft Tumor Model Human xenograft tumor models are utilized to assess the efficacy of anti-cancer agents against human tumor cells in immunocomprimized mice. Subcutaneous xenografts of the human Burkitt lymphoma Ramos growing in nude mice are used to demonstrate the anti-tumor effect of a combination of anti-CD37 mAb (mAb A2) in combination with the chemotherapy regimen ICE (ifosfamide, carboplatin, etoposide). The following study design is applied:

| Group | Number of mice | Compound | Dose [mg/kg] | Schedule [days of admin. per week] | Route |
|---|---|---|---|---|---|
| 1 | 8 | NaCl (0.9%) | — | d1, d2, d3 | i.p. |
| 2 | 7 | Ifosfamide | 83.3 | d1, d2, d3 | i.p. |
|   |   | Carboplatin | 7.8 | d1, d2, d3 | i.p. |
|   |   | Etoposide | 0.5 | d1, d2, d3 | i.p. |
| 3 | 7 | A2 | 1.0 | d1, d4 | i.v. |
|   |   | Ifosfamide | 83.3 | d1, d2, d3 | i.p. |
|   |   | Carboplatin | 7.8 | d1, d2, d3 | i.p. |
|   |   | Etoposide | 0.5 | d1, d2, d3 | i.p. |
| 4 | 7 | A2 | 1.0 | d1, d4 | i.v. |

During the 15 day treatment period, control tumours grow from a median volume of 76 mm$^3$ to a volume of 1084 mm$^3$ Treatment with ICE administered three times weekly i.p. for two weeks significantly delays tumour growth (median TGI=65%, p=0.0012). A tumor volume of 500 mm$^3$ is reached after 15 days, a significant difference compared to controls (p=0.0093).

Treatment with 1 mg/kg mAb A2 twice weekly i.v. for two weeks significantly delays tumour growth (median TGI=70%, p=0.0012). A tumor volume of 500 mm$^3$ is reached after 16 days, a significant difference compared to controls (p=0.0093).

Treatment with the combination of A2 and ICE significantly delays tumour growth (median TGI=84%, p=0.0009). A tumor volume of 500 mm$^3$ is still not reached on day 24, the last day of the study (p=0.0050).

Two cycles of therapy with a combination of A2 and ICE show improved efficacy (TGI=84%) compared to single agent treatment with A2 (TGI=70%) or with ICE (TGI=65%). Combination therapy delays tumor progression (time until the group median tumor volume exceeded 500 mm$^3$) compared to single-agent mAb A2 (>24 days versus 16 days, p=0.0469) and compared to ICE alone (>24 versus 15 days, p=0.0690).

In the present study, two cycles of treatment with A2 at a suboptimal dose of 1 mg/kg twice weekly significantly delays tumor growth (TGI=70%). For treatment with ICE, the ratio of ifosfamide, carboplatin and etoposide is selected according to the ratio used in humans, and the dose level selected represents the MTD as determined in previous studies. ICE treatment results in significant efficacy (TGI=65%) and is well tolerated. Two cycles of combination therapy with ICE and A2 show improved efficacy (TGI=84%) compared to single-agent treatment.

After termination of the control group due to large tumor size (day 15), the remaining animals receive a third cycle of therapy, and efficacy is determined by calculating the time elapsed until a median tumor volume of 500 mm³ is exceeded. This endpoint is reached by the single-agent treatment groups on days 15 and 16, respectively, whereas the combination group median is still below the endpoint volume on day 24, the last day of the experiment. Statistically, this difference is significant with respect to single agent A2 (p=0.0469).

In conclusion the mAb A2 administered as a single agent significantly inhibits growth of Ramos lymphomas. Addition of A2 to ICE chemotherapy improves efficacy, the combination is superior to single-agent A2 Improved efficacy of a combination of A2 and ICE chemotherapy is indicative for additive or synergistic effects of such a combination. An improved anti-tumor efficacy of a combination treatment of A2 and ICE provides a potential clinical benefit over monotherapy for patients suffering from CD37-positive malignancies.

What is claimed is:

1. A method for the treatment of a patient suffering from chronic lymphocytic leukemia (CLL) or B-cell non-Hodgkin's lymphoma (B-NHL), the method comprising administering to the patient (a) a CD37 antibody and (b) a combination chemotherapy regimen comprising ICE (ifosfamide, carboplatin, and etoposide (or etoposide phosphate)), whereby the CD37 antibody comprises:
   a) a variable heavy chain comprising CDRs having the SEQ ID NOs: 15, 16 or 21, and 17, and
   b) a variable light chain comprising CDRs having the SEQ ID NOs: 18, 19 and 20.

2. The method of claim 1, wherein the patient receives at least one dose of the CD37 antibody and at least one administration of ICE during a treatment cycle, whereby a treatment cycle is a time period of about 1 to 6 weeks.

3. The method of claim 1, wherein the patient additionally receives at least one dose of a CD20 antibody which is Rituximab.

4. The method of claim 1, whereby the CD37 antibody is administered to said patient simultaneously with the administration of ICE.

5. The method of claim 1, whereby the CD37 antibody is administered to said patient after the administration of ICE.

6. The method of claim 1, whereby the CD37 antibody is administered to said patient before the administration of ICE.

7. The method of claim 2, whereby the CD37 antibody is administered at least twice during the treatment cycle, whereby one of the administrations of the CD37 antibody is in the middle of the treatment cycle at about 2 weeks or once weekly.

8. The method of claim 1, whereby the CD37 antibody is administered in a dose of about 10 µg/kg to 40 mg/kg or in a dose of about 1 mg and 2800 mg per patient.

9. The method of claim 1, wherein the patient is a 70 kg human patient, wherein the said human patient is administered a weekly dose in the range of 1 mg to 2800 mg, whereby the CD37 antibody comprises SEQ ID NOs: 5 and 6.

10. The method of claim 1, wherein the patient is a 70 kg human patient, wherein the said human patient is administered a weekly dose in the range of 1 mg to 2800 mg, whereby the CD37 antibody comprises SEQ ID NOs: 11 and 12.

11. The method of claim 2, whereby doses of each component of ICE are:
   i) for ifosfamide between 3-7 g/m$^2$ body surface, whereby the ifosfamide is administered on the $2^{nd}$ treatment day of the treatment cycle,
   ii) for carboplatin between 200-800 mg, whereby the carboplatin is administered on the $2^{nd}$ treatment day of the treatment cycle and
   iii) for etoposide between 50-200 mg/m$^2$, whereby the etoposide is administered on the $1^{st}$, $2^{nd}$ and $3^{rd}$ treatment day of the treatment cycle.

12. The method of claim 11, whereby the patient is a patient suffering from B-NHL and whereby the treatment cycle is preferably 2-3 weeks.

13. The method of claim 1, whereby the combination of the CD37 antibody and ICE is administered as first line treatment.

14. The method of claim 1, whereby the combination of the CD37 antibody and ICE is administered as second or later line treatment.

15. A method of reducing CD37-positive cells comprising:
a) Exposing CD37-positive cells to a CD37 antibody and
b) Exposing CD37-positive cells to ICE (ifosfamide, carboplatin, and etoposide (or etoposide phosphate)),
whereby said CD37 antibody of step a) comprises:
i) a variable heavy chain comprising CDRs having the SEQ ID NOs: 15, 16 or 21, and 17, and
ii) a variable light chain comprising CDRs having the SEQ ID NOs: 18, 19 and 20.

16. The method of claim 15, whereby the CD37-positive cells are additionally exposed to a CD20 antibody which is Rituximab.

17. The method of claim 15, whereby the CD37-positive cells are exposed to the CD37 antibody and ICE simultaneously, or
whereby the CD37-positive cells are exposed to the CD37 antibody after they are exposed to ICE, or
whereby the CD37-positive cells are exposed to the CD37 antibody before they are exposed to ICE, preferably within 24 hrs or within 36 hrs before they are exposed to ICE.

18. A kit for reducing CD37-positive cells comprising:
a) a container comprising a CD37 antibody, whereby said CD37 antibody comprises:
i) a variable heavy chain comprising CDRs having the SEQ ID NOs: 15, 16 or 21, and 17, and
ii) a variable light chain comprising CDRs having the SEQ ID NOs: 18, 19 and 20, and
b) a protocol for using the kit to reduce CD37-positive cells by administration of the CD37 antibody of step a) in combination with ICE (ifosfamide, carboplatin, and etoposide (or etoposide phosphate)) and/or
c) optionally a protocol for using the kit to reduce CD37-positive cells by administration of the CD37 antibody of step a) in combination with ICE and a CD20 antibody which is Rituximab.

19. An article of manufacture comprising a CD37 antibody, ICE (ifosfamide, carboplatin, and etoposide (or etoposide phosphate)), and a label indicating a method according to claim 15, whereby the said CD37 antibody comprises:
a) a variable heavy chain comprising CDRs having the SEQ ID NOs: 15, 16 or 21, and 17, and
b) a variable light chain comprising CDRs having the SEQ ID NOs: 18, 19 and 20.

20. A pharmaceutical composition comprising a CD37 antibody, ICE (ifosfamide, carboplatin, and etoposide (or etoposide phosphate)), and a pharmaceutically acceptable carrier, whereby the CD37 antibody comprises:
a) a variable heavy chain comprising CDRs having the SEQ ID NOs: 15, 16 or 21, and 17, and
b) a variable light chain comprising CDRs having the SEQ ID NOs: 18, 19 and 20.

21. A method of treating a CD37-positive malignancy, comprising administrating a therapeutically effective amount of i) a CD37 antibody and ii) ICE (ifosfamide, carboplatin, and etoposide (or etoposide phosphate)) and optionally iii) a CD20 antibody which is Rituximab to a patient in need thereof, whereby the CD37 antibody comprises:
a) a variable heavy chain comprising CDRs have the SEQ ID NOs: 15, 16 or 21, and 17, and
b) a variable light chain comprising CDRs having the SEQ ID NOs: 18, 19 and 20.

22. The method of treatment according to claim 21, whereby the CD37-positive malignancy is selected from the group consisting of: multiple myeloma, plasmacytoma, T-cell lymphoma, acute lymphoblastic leukemia (ALL), and B-cell malignancies, e.g. B-cell lymphomas, aggressive B-cell lymphoma, Hodgkin's disease, B-cell non-Hodgkin's lymphoma (B-NHL), lymphomas, Waldenström's macroglobulinaemia (also called lymphoplasmacytic lymphoma or immunocytoma), central nervous system lymphomas, leukemias, acute lymphoblastic leukemia (ALL), chronic lymphocytic leukemia (CLL; also termed B-cell chronic lymphocytic leukemia B-CLL), hairy cell leukemia, chronic myoblastic leukemia), small lymphocytic lymphoma, B-cell prolymphocytic leukemia, lymphoplasmacytic lymphoma, splenic marginal zone lymphoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, grey zone lymphoma, B-cell proliferations of uncertain malignant potential, lymphomatoid granulomatosis, and post-transplant lymphoproliferative disorder.

23. The method of claim 22, whereby the B-cell malignancy is B-cell non-Hodgkin's lymphoma, B-cell chronic lymphocytic leukemia, and whereby the B-cell malignancy is B-cell non-Hodgkin's lymphoma.

\* \* \* \* \*